US00PP28970P2

(12) United States Plant Patent
Benetka

(10) Patent No.: US PP28,970 P2
(45) Date of Patent: Feb. 20, 2018

(54) ***WEIGELA* PLANT NAMED 'VUKOZ90345'**

(50) Latin Name: *Weigela hybrida*
Varietal Denomination: VUKOZ90345

(71) Applicant: Vojtech Benetka, Chodov (CZ)

(72) Inventor: Vojtech Benetka, Chodov (CZ)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,316

(22) Filed: Sep. 2, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne M Grunberg
(74) *Attorney, Agent, or Firm* — Cassandra Bright

(57) ABSTRACT

A new and distinct *Weigela* plant named 'VUKOZ90345' is disclosed, characterized by abundant pink flowers and plants which re-bloom. The new variety is a *Weigela*, normally produced as an outdoor garden plant.

3 Drawing Sheets

Latin name of the genus and species: *Weigela hybrida.*
Variety denomination: 'VUKOZ90345'.

BACKGROUND OF THE INVENTION

The new *Weigela* cultivar is a product of a planned breeding program conducted by the inventor, Vojtech Benetka in Pruhonice, Czech Republic. The objective of the breeding program was to produce new *Weigela* varieties with a low growth habit. The cross resulting in this new variety was made in 1990.

The seed parent is the unpatented *Weigela* 'Eva Supreme'. The pollen parent is the unpatented, proprietary *Weigela* '87-8-1'. The new variety was identified as a potentially interesting selection in 1994, at a research nursery in Pruhonice, Czech Republic.

Asexual reproduction of the new cultivar 'VUKOZ90345' by softwood cuttings was first performed in 1994, at a research nursery in Pruhonice, Czech Republic. Subsequent propagation has shown that the unique features of this cultivar are stable and reproduced true to type in five successive generations.

SUMMARY OF THE INVENTION

The cultivar 'VUKOZ90345' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VUKOZ90345' These characteristics in combination distinguish 'VUKOZ90345' as a new and distinct *Weigela* cultivar:

1. Pink flowers.
2. Rich flowering.
3. Re-blooming of flowers.

PARENT COMPARISON

Plants of the new cultivar 'VUKOZ90345' are similar to plants of the seed parent in most horticultural characteristics, however, plants of the new cultivar 'VUKOZ90345' differ in the following;

1. New cultivar has pink flowers, whereas the seed parent has crimson flowers.

Plants of the new cultivar 'VUKOZ90345' are similar to plants of the pollen parent in most horticultural characteristics, however, plants of the new cultivar 'VUKOZ90345' differ in the following;

1. New cultivar has pink flowers, whereas the parent has dark pink flowers.

COMMERCIAL COMPARISON

Plants of the new cultivar 'VUKOZ90345' can be compared to the patented commercial variety *Weigela* 'Bokrasopea' (U.S. Plant Pat. No. 24,585). These varieties are similar in most horticultural characteristics; however 'VUKOZ90345' differs in the following:

1. New cultivar has lighter pink flowers than this comparator.
2. New cultivar has larger flowers than this comparator.

BRIEF DESCRIPTION OF THE PHOTOGRAPHS

The accompanying photograph in FIG. 1 illustrates in full color a typical plant of 'VUKOZ90345' grown in a 2 gallon container.

Figure 1:
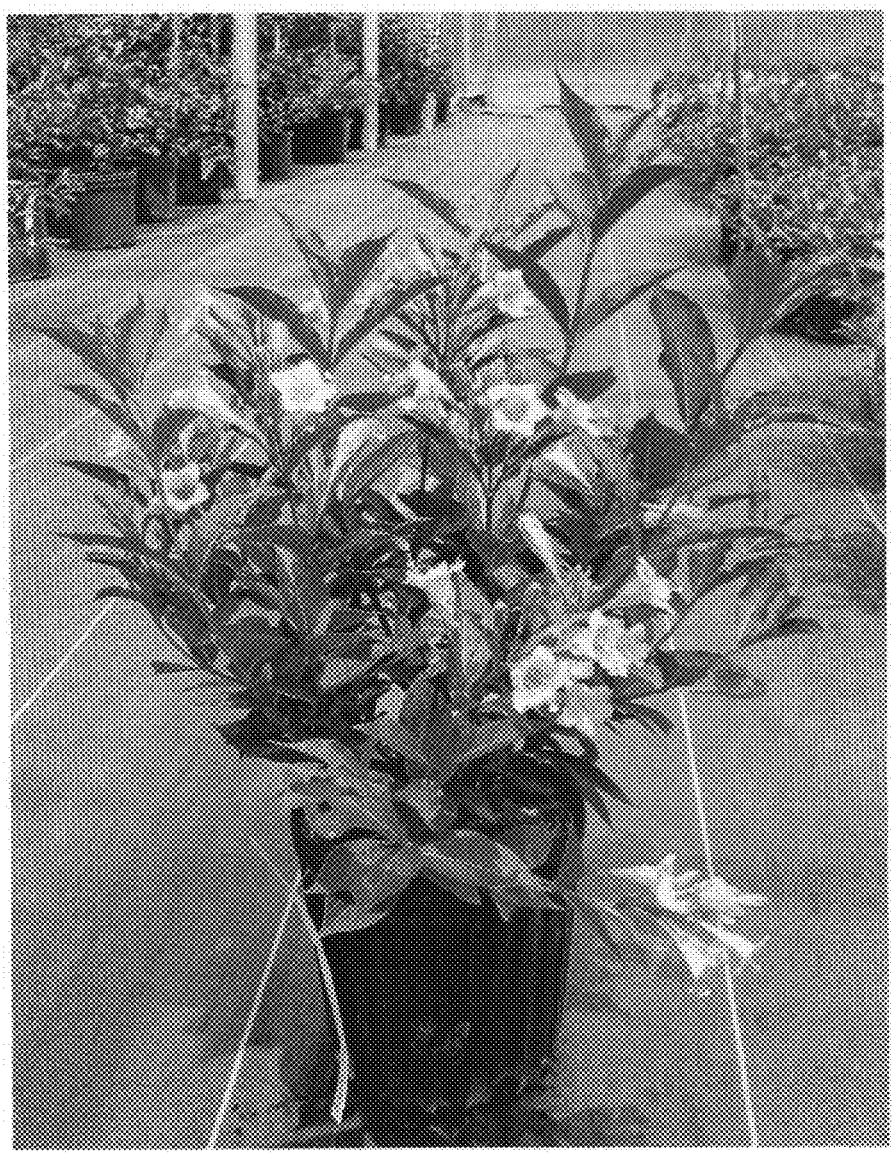
Figure 2:
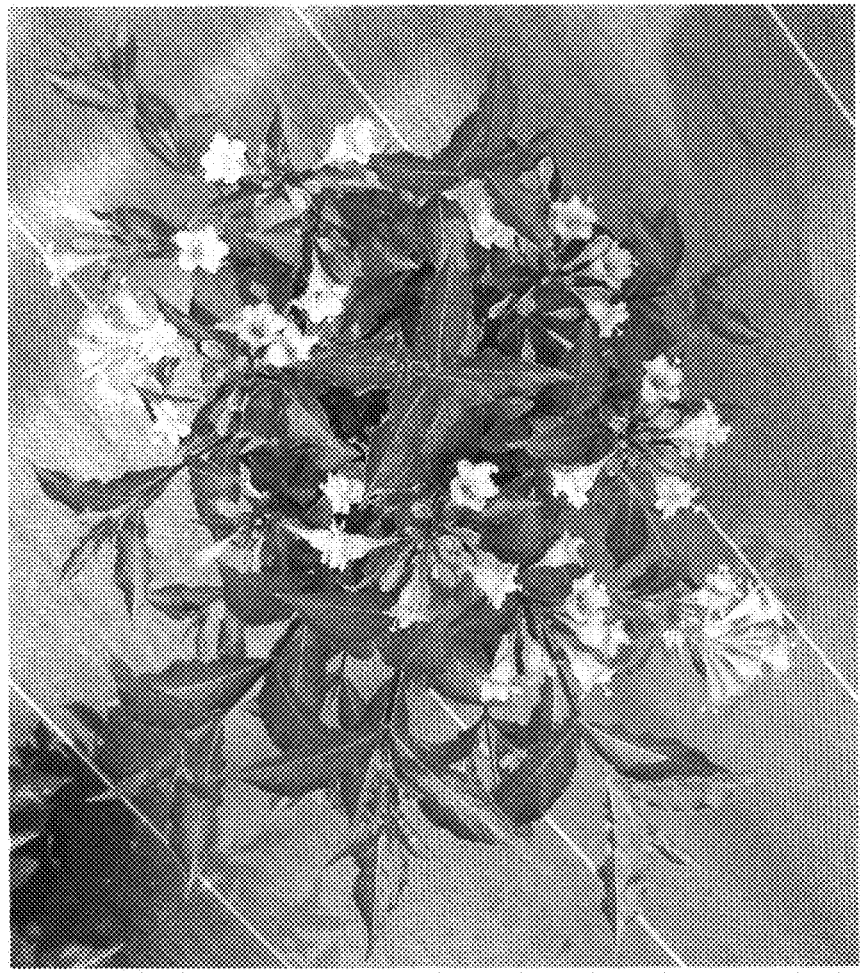
FIG. 2 illustrates a top view of the same plant. Age of the plant photographed is approximately 2 years.
Figure 3:
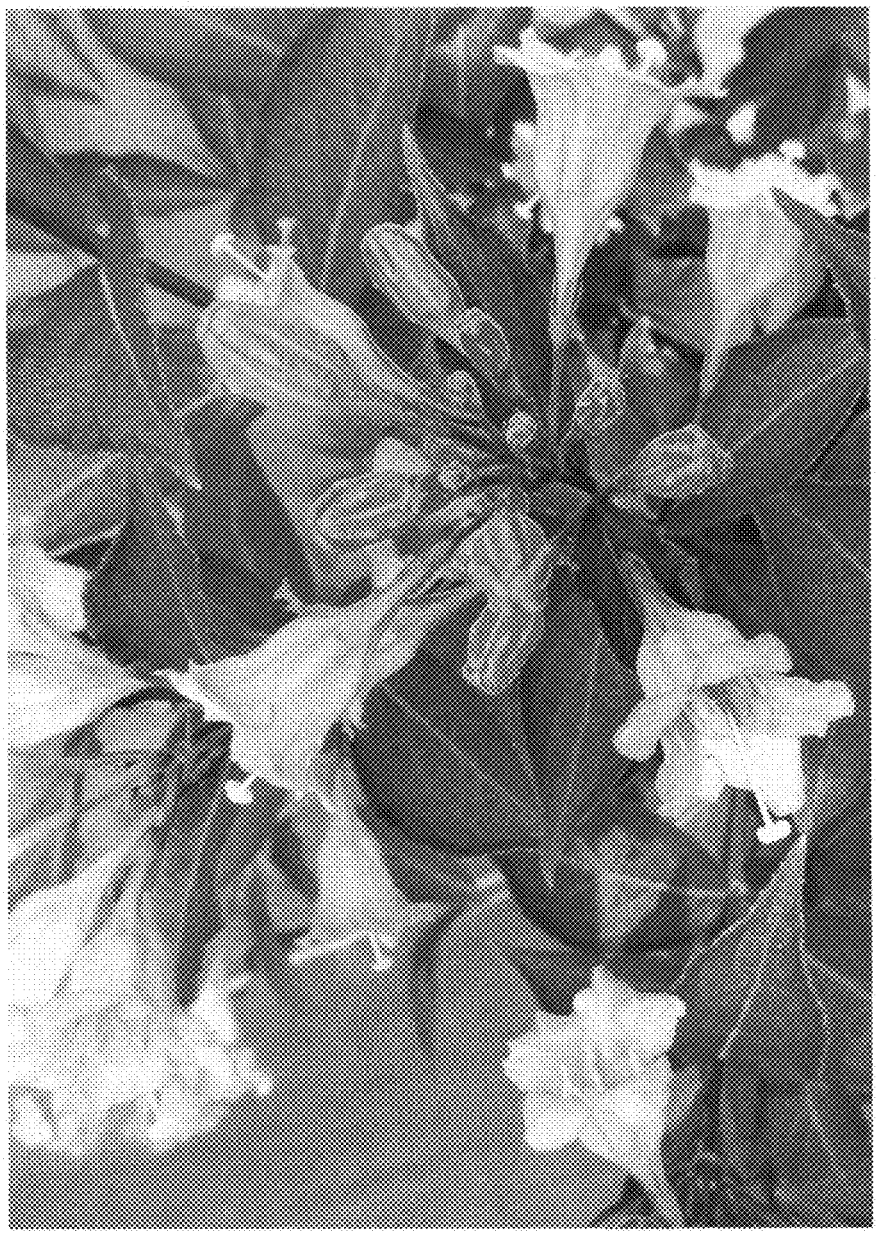
FIG. 3 illustrates a close up view of flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'VUKOZ90345' plants grown in a polyhouse in Grand Haven, Mich. Measurements were taken during late Spring. The plants were 2 years old. The growing temperature ranged from approximately 5° C. to 27° C. Measurements and numerical values represent averages of typical plant types.

Botanical classification: *Weigela hybrida* 'VUKOZ90345'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.
Age of plant described: Approximately 2 years old.
Growth habit: Medium, compact growth.
Pot size of plant described: 2 gallon container.
Overall plant shape: Upright and rounded.
Height: 76 cm.
Plant spread: 82 cm.
Growth rate: Medium.
Plant vigor: Strong.
Branching characteristics: Opposite.
Length of primary lateral branches: Average 64 cm.
Diameter of lateral branches: 8.0 mm.
Quantity of lateral branches: 25.
Stem:
- *Stem appearance*.—Round.
- *Stem strength*.—Good.
- *Color*.—Near RHS Yellow-Green 146B blended with RHS Greyed-Brown 199A.
- *Pubescence*.—Yes.

Internode length: Range is 3.3 to 4.3 cm.

FOLIAGE

Leaf:
- *Arrangement*.—Opposite.
- *Leaf shape*.—Ovate-oblanceolate.
- *Average length*.—Approximately 5.5 cm.
- *Average width*.—Approximately 2.5 cm.
- *Apex*.—Acute.
- *Base*.—Rounded.
- *Margin*.—Serrulate.
- *Texture of top surface*.—Slight pubescence.
- *Texture of bottom surface*.—Pubescent, to a greater extent than upper surface.
- *Color*.—Young foliage upper side: Near RHS Green 137A. Young foliage under side: Near RHS Green 138B. Mature foliage upper side: Near RHS Green 137A. Mature foliage under side: Near RHS Green 138B.
- *Venation*.—Pattern: Pinnate. Color upper side: Near RHS Yellow-Green 145A. Color under side: Near RHS Yellow-Green 145C.
- *Petiole*.—Length: 2.5 mm. Diameter: 1.5 mm. Petiole color upper side: Near RHS Yellow-Green 145A. Petiole color lower side: Near RHS Yellow-Green 145C. Petiole Texture: Pubescent.
- *Foliage durability*.—Very durable.

FLOWER

Natural flowering season: Late spring to summer.
Inflorescence type and habit: Umbel to panicle.
Inflorescence height: 8.0 cm.
Inflorescence width: 6.0 cm.
Quantity of flowers per inflorescence: 18 to 22.
Quantity of flowers per plant: Hundreds.
Individual flowers:
- *Flower shape*.—Salverform.
- *Flower aspect*.—Upward and slightly outward.
- *Flowering arrangement*.—Single salverform flower.
- *Size*.—Diameter: Approximately 2.2 cm. Depth: Approximately 3.0 cm.
- *Flower other characteristics*.—Persistence: Self cleaning. Fragrance: Slight sweet scent.

Bud:
- *Shape*.—Obovate to spatulate.
- *Length*.—2.8 cm.
- *Diameter*.—8.0 mm.
- *Color*.—Near RHS Red-Purple 63A fading to near RHS Red-Purple 63B towards the base of the bud.

Petal:
- *Petal arrangement*.—Whorled, fused at opening of throat.
- *Number of petals per flower*.—5.
- *Petal shape*.—Obovate to oblanceolate.
- *Petal base*.—Fused at throat.
- *Margin*.—Entire, slightly undulate.
- *Tip shape*.—Obtuse.
- *Length*.—1.0 cm.
- *Width*.—0.8 cm.
- *Texture*.—Upper: Smooth. Lower: Smooth.
- *Flower tube*.—Length: 3.0 cm. Diameter, base: 2.0 mm. Color: near RHS Red-Purple 66C.
- *Throat*.—Texture: Smooth. Color: near RHS Red-Purple 66C.

Petal color:
- *When opening*.—Upper surface: Near RHS Red-Purple 63C. Lower surface: Near RHS Red-Purple 63B.
- *Fully opened*.—Upper surface: Near RHS Red-Purple 63B with edges near RHS Red-Purple 63D. Lower surface: Near RHS Red-Purple 70C blended with near RHS Red-Purple 66C.
- *Fades to*.—Near RHS Red-Purple 63B with edges near RHS Brown 200C.

Sepal:
- *Arrangement*.—Unguiculate, fused at base.
- *Appearance*.—Long, narrowly triangular.
- *Number*.—5.
- *Shape*.—Narrowly triangular.
- *Tip*.—Acute.
- *Base*.—Obtuse.
- *Margin*.—Entire.
- *Length*.—7 mm.
- *Width*.—1 mm.
- *Texture, upper*.—Smooth, coriaceous.
- *Texture, lower*.—Smooth, coriaceous.
- *Color*.—Upper surface at maturity: Near RHS Yellow-Green 145B blended with near RHS Yellow-Green 146B. Under surface at maturity: Near RHS Yellow-Green 145B blended with near RHS Red-Purple 63A.

Peduncle:
*Length.*—1.0 cm.
*Diameter.*—1.5 mm.
*Color.*—Near RHS Green 143C.
*Orientation.*—Upright and outward.
*Strength.*—Good.
*Texture.*—Smooth, coriaceous, slightly pubescent.
Pedicel:
*Length.*—1.9 cm.
*Diameter.*—1.5 mm.
*Angle.*—Upright and outward.
*Strength.*—Good.
*Texture.*—Smooth, coriaceous, slightly pubescent.
*Color.*—Near RHS Green 143C.

REPRODUCTIVE ORGANS

Stamens:
*Number.*—5.
*Filament length.*—2.7 cm.
*Filament color.*—Near RHS White 155B.
Anthers:
*Shape.*—Linear, slightly oblong.
*Length.*—5 mm.
*Color.*—Near RHS White 155B.
*Pollen color.*—Near RHS White 155B.
*Pollen amount.*—Some.
Pistil:
*Number.*—1 per flower.
*Length.*—4.0 cm.
*Stigma.*—Color: Near RHS White 155B. Shape: Globular, flat-bottomed.
*Style.*—Length: 3.9 cm. Color: Near RHS White 155B.

OTHER CHARACTERISTICS

Seeds and fruits: Not observed.
Disease/pest resistance: Neither resistance nor susceptibility to normal diseases and pests of *Weigela* have been observed aside from mildew resistance.
Temperature tolerance: The new variety tolerates temperatures between −31° C. to 38° C.
Environmental stressors: Good resistance to wind and rain.

What is claimed is:

1. A new and distinct cultivar of *Weigela hybrida* plant named 'VUKOZ90345' as herein illustrated and described.

* * * * *